United States Patent
Fernandes et al.

(10) Patent No.: US 9,267,853 B2
(45) Date of Patent: Feb. 23, 2016

(54) DEVICE AND METHODS FOR TEMPERATURE AND HUMIDITY MEASUREMENTS USING A NANOCOMPOSITE FILM SENSOR

(71) Applicant: Brown University, Providence, RI (US)

(72) Inventors: Gustavo E. Fernandes, Providence, RI (US); Jingming Xu, Providence, RI (US); Jin Ho Kim, Warwick, RI (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 14/138,528

(22) Filed: Dec. 23, 2013

(65) Prior Publication Data

US 2014/0105242 A1    Apr. 17, 2014

Related U.S. Application Data

(63) Continuation of application No. PCT/US2012/043829, filed on Jun. 22, 2012.

(60) Provisional application No. 61/500,240, filed on Jun. 23, 2011.

(51) Int. Cl.

| | |
|---|---|
| *C08K 3/22* | (2006.01) |
| *G01N 25/00* | (2006.01) |
| *G01K 7/16* | (2006.01) |
| *G01J 5/04* | (2006.01) |
| *G01N 27/12* | (2006.01) |
| *G01J 5/02* | (2006.01) |
| *G01J 5/20* | (2006.01) |
| *B29C 39/00* | (2006.01) |
| *B32B 38/00* | (2006.01) |
| *B82Y 15/00* | (2011.01) |

(52) U.S. Cl.
CPC ............... *G01K 7/16* (2013.01); *B29C 39/003* (2013.01); *B32B 38/00* (2013.01); *G01J 5/023* (2013.01); *G01J 5/046* (2013.01); *G01J 5/20* (2013.01); *G01N 27/121* (2013.01); *G01N 27/127* (2013.01); *B82Y 15/00* (2013.01)

(58) Field of Classification Search
USPC ............................................ 524/431; 374/45
See application file for complete search history.

(56) References Cited

U.S. PATENT DOCUMENTS

| 8,158,005 B1 * | 4/2012 | Gupta et al. ................... 210/668 |
| 2008/0241262 A1 * | 10/2008 | Lee et al. ....................... 424/490 |

OTHER PUBLICATIONS

Aliev, Infrared Physics & Technology, 51, 541-545, 2008.*
Zhao et al., New Journal of Chemistry, 30, 915-920, 2006.*
Aliev (2008) "Bolometric detector on the basis of single-wall carbon nanotube/polymer composite", Infrared Physics & Technology 51: 541-545.
International Search Report and Written Opinion of the International Searching Authority received in PCT/US12/043829, mailed Feb. 27, 2013 (13 pages).
Barrau et al. (2003) "DC and AC conductivity of carbon nanotubes-polyepoxy composites", Macromolecules 36: 5187-5194.
Connor et al. (1998) "Broadband ac conductivity of conductor-polymer composites", Physical Review B 57, 2286-2294.
Dalton et al. (1999) "Optical Absorption and Fluorescence of a Multi-walled Nanotube-Polymer Composite", Synthetic Metals 102: 1176-1177.
Garner et al. (2009) "Refractive Index Change Due to Volume-Phase Transition in Polyacrylamide Gel Nanospheres for Optoelectronics and Bio-photonics", Applied Physics Express 2: 057001-057004.
Gracheva et al. (2010) "Molecular basis of infrared detection by snakes", Nature 464: 1006-U1066 (7pgs).
Map of Life (2008) "Infrared Detection in Snakes", at http://www.mapoflife.org/topics/topic_312_infrared-detectionin-snakes/.
Itkis et al. (2002) "Spectroscopic study of the Fermi level electronic structure of single-walled carbon nanotubes", Nano Letters, 2(2):155-159.
Itkis et al. (2006) "Bolometric infrared photoresponse of suspended single-walled carbon nanotube films", Science 312: 413-416.
Jakubinek et al. (2010) "Temperature dependence of thermal conductivity enhancement in single-walled carbon nanotube/polystyrene composites", Applied Physics Letters 96: 083105-083108.
Kataura et al. (1999) "Optical properties of single-wall carbon nanotubes", Synthetic Metals 103:2555-2558.
Kolobov et al. (2004) "Understanding the phase-change mechanism of rewritable optical media", Nat Mater 3: 703-708.
Kymakis et al. (2002) "Single-walled carbon nanotube—polymer composites: electrical, optical and structural investigation", Synthetic Metals, 127:59-62.
Liddiard (1984) "Thin-Film Resistance Bolometer Ir Detectors", Infrared Phys 24: 57-64.
Lu et al. (2008) "Effects of thermal annealing on noise property and temperature coefficient of resistance of single-walled carbon nanotube films", Applied Physics Letters, 93: 213101-213104.
Lu et al. (2009) "Suspending single-wall carbon nanotube thin film infrared bolometers on microchannels", Applied Physics Letters 94, 163110 (4 pgs.).

(Continued)

*Primary Examiner* — Hui Chin
(74) *Attorney, Agent, or Firm* — Lawson & Weitzen, LLP; Sonia K. Guterman; Michael I. Falkoff

(57) ABSTRACT

Devices and methods are provided for a nanocomposite having a phase change polymer matrix and conductive nanoparticles to provide greatly enhanced responsivity to temperature and/or humidity. A sensing film includes carbon nanotubes (CNTs) and the polymer. Operation near the transition temperature increases the TCR by over an order of magnitude, thus providing a new platform for devices such as IR sensors, bolometers and imaging elements, MEMS devices, compensating or uncompensated circuit elements and other electronic devices. Nanocomposite films may be under about one micron thick, and coatings, constant environment chambers or mounts, and other engineered improvements and variations may be provided to further enhance the response, range, response times or sensitivity of the film-based devices. One embodiment employs a nanocomposite film under one micron in thickness to operate as an uncooled but highly sensitive infrared bolometer under ambient conditions.

11 Claims, 10 Drawing Sheets

(56) References Cited

OTHER PUBLICATIONS

Lu et al. (2010) "High performance multiwall carbon nanotube bolometers", Journal of Applied Physics 108: 084305-084310.

Morin (1959) "Oxides Which Show a Metal-to-Insulator Transition at the Neel Temperature", Physical Review Letters 3: 34-36.

Zhang et al. (2006) "Transparent, conductive, and flexible carbon nanotube films and their application in organic light-emitting diodes", Nano Letters 6: 1880-1886.

Pradhan et al. (2008) "Carbon nanotube—Polymer nanocomposite infrared sensor", Nano Letters 8: 1142-1146.

Sankapal et al. (2007) "Electrical properties of air-stable, iodine-doped carbon-nanotube-polymer composites", Applied Physics Letters 91: 173103-173106.

Schild (1992) "Poly (N-Isopropylacrylamide)—Experiment, Theory and Application", Progress in Polymer Science 17: 163-249.

Sheng et al. (1978) "Fluctuation-Induced Tunneling Conduction in Carbon-Polyvinylchloride Composites", Physical Review Letters 40: 1197-1200.

Suarez et al. (2006) "Swelling kinetics of poly(N-isopropylacrylamide) minigels", Journal of Physical Chemistry B 110: 25729-25733.

Subrahmanyam et al. (2008) "Nano-vanadium oxide thin films in mixed phase for microbolometer applications", Journal of Physics D: Applied Physics 41: 195108 (6pgs.).

Takahashi et al. (2004) "Swelling and deswelling kinetics of poly(N-isopropylacrylamide) gels", Journal of Chemical Physics 120: 2972-2979.

Tarasov et al. (2007) "Carbon nanotube bolometers", Applied Physics Letters 90: 163503-163506.

Yanagi et al. (2010) "Transport Mechanisms in Metallic and Semi-conducting Single-Wall Carbon Nanotube Networks", Acs Nano 4(7): 4027-4032.

Zadrazil et al. (2010) "Investigation of thermo-responsive optical properties of a composite hydrogel", Colloids and Surfaces a: Physicochem. Eng. Aspects 372: 115-119.

\* cited by examiner

Table I

| Sample | Description | Composition | CNT mass fraction |
|---|---|---|---|
| R | CNT film, ~ 10 nm thick | 1 ml (0.005 mg/ml) CNT | 1 |
| A | CNT-PNIPAM film | 1 ml (2.5 mg/ml) CNT + 1 ml (50 mg/ml) PNIPAM | 0.05 |
| D (1-4) | CNT-PNIPAM films with varying CNT mass fraction | D1 – 1 ml (0.001 mg/ml) CNT + 1 ml (10 mg/ml) PNIPAM<br>D2 – 1 ml (0.002 mg/ml) CNT + 1 ml (10 mg/ml) PNIPAM<br>D3 – 1 ml (0.005 mg/ml) CNT + 1 ml (10 mg/ml) PNIPAM<br>D4 – 1 ml (0.01 mg/ml) CNT + 1 ml (10 mg/ml) PNIPAM | D1-$10^{-4}$<br>D2-$2\times10^{-4}$<br>D3-$5\times10^{-4}$<br>D4-$10^{-3}$ |

Figure 3C

DEVICE AND METHODS FOR TEMPERATURE AND HUMIDITY MEASUREMENTS USING A NANOCOMPOSITE FILM SENSOR

RELATED APPLICATIONS

The present application is a continuation of international application serial number PCT/US12/43829 filed Jun. 22, 2012 which claims the benefit of U.S. provisional application Ser. No. 61/500,240 filed Jun. 23, 2011, each of which is incorporated herein by reference in its entirety.

GOVERNMENT FUNDING

This invention was made with government support under FA9550-09-1-0296 awarded by the Air Force Office of Scientific Research and W911NF-08-G-0224 awarded by the Army Research Office. The government has certain rights in the invention.

TECHNICAL FIELD

Sensing devices and methods are provided wherein a phase change polymer and conductive nanoparticles form a nanocomposite film that has enhanced response and sensitivity for sensing temperature and/or humidity. The polymer magnifies a measurable characteristic (e.g., the temperature coefficient of resistance) of conductive paths defined by the nanoparticles in the nanocomposite material. Sensitivity of a hygrometer or bolometer formed of the material is improved by an order of magnitude or more by selection of the polymer and the nanoparticles, and may be tailored to operate without extrinsic cooling in a specific temperature range.

BACKGROUND

Percentage change in resistivity of a material or component resulting from a unit change in temperature, or the temperature coefficient of resistance (TCR), is a figure of merit for thermal sensing applications, and in thin film bolometers based on film temperature the responsivity is found to be directly proportional to the TCR. To achieve the best possible bolometric responsivity, different material platforms have been explored, and in research carbon nanotube films and carbon nanotube-polymer nanocomposites have been proposed for bolometric infrared detection based on their characteristics of high optical absorbance, low thermal mass, high strength and elasticity, light weight and potentially low cost synthesis processing. Aliev., Infrared Physics & Technology, 51: 541-54, 2008; Itkis et al., Science, 312:413-416, 2006; Lu et al., Journal of Applied Physics, 108:084305-084310; Tarasov et al., Applied Physics Letters, 90: 163503-163506; Itkis et al., Nano Letters, 2:155-159, 2002; Kataura et al., Synthetic Metals, 103:2555-2558, 1999; Kymakis et al., Synthetic Metals, 127:59-62, 2002, Dalton et al., Synthetic Metals, 102:1176-1177, 1999.

However, the room temperature TCR values for carbon nanotubes and carbon nanotube-polymer nanocomposites have not surpassed the −0.5%/° C. mark [negative 0.5 percent per ° C.]. Aliev, Ibid.; Itkis et al., Ibid.; Jakubinek et al., Applied Physics Letters, 96: 083105-083108, 2010; Lu et al., Applied Physics Letters, 93:213101-213104, 2008; Tarasov et al., Ibid. These low TCR values place stringent requirements on device engineering and thermal management to achieve adequate responsivities, and to offset potential cost and weight benefits offered by carbon nanotube-based platforms. Reports describing carbon nanotube film bolometers show only adequate performances at pressures in the milli-Torr range with substantial or total loss of responsivity at room pressure, at which thermal coupling of the low mass film with its surroundings is much greater.

There is a need for devices and methods for configuring a nanoparticle sensing element to result in high TCR, such that enhanced uncooled IR bolometric detection can be readily observed in its as-is thin-film form, before applying any packaging or thermal engineering strategies.

SUMMARY

An embodiment of the invention provides a nanocomposite material comprising at least a nanoparticle component, such as a carbon nanotubes (CNTs) and a non-conductive polymer, such as a hydrogel polymer, wherein the polymer experiences a reversible phase change in the vicinity of an operating region of interest. The phase change may be a hydrophobic/hydrophilic phase transition in response to at least one of a temperature change and a humidity change. In an embodiment of the nanocomposite, the non-conductive polymer comprises the hydrogel poly(N-isopropylacrylamide), referred to as PNIPam.

Another embodiment of the invention provides a method of preparing a nanocomposite film comprising quantum dots or other nanoparticles, such as carbon nanotubes (CNTs) and a non-conductive hydrogel polymer that experiences a reversible hydrophobic/hydrophilic phase transition in response to temperature change or a humidity change. An embodiment of the method includes the steps of: mixing water dispersed CNTs containing sodium dodecyl sulphate (SDS) with an aqueous solution of the non-conductive hydrogel polymer containing SDS; vacuum filtering through a membrane filter and forming a nanocomposite film of the nanoparticles and polymer; and forming contacts so that the nanocomposite film extends between the electrodes for circuit connection to measure electrical resistance of the film, thus preparing the nanocomposite film sensor element.

In an embodiment of this method, the concentration of CNTs or other conductive nanoparticles is less than about 0.05%, about 0.025%, or about 0.0125%. In an embodiment of this method, the non-conductive phase change polymer is a hydrogel, poly(N-isopropylacrylamide) referred to as PNIPam. In an embodiment of the method of preparing nanocomposite film, the SDS concentration in the dispersion of CNT in water and in the aqueous solution of non-conductive hydrogel polymer is about 1%. In an embodiment of this method a high degree of uniformity in the nanocomposite film is observed and an absence or reduced clumping or bundling of CNTs or aggregation of polymer, as determined by scanning electron microscopy (SEM) or atomic force microscopy (AFM). In an embodiment of this method forming the contacts for measuring resistance may include applying metal by masked electron beam evaporation, or using conductive paste to attach wire contacts to the film. Another embodiment of this method includes, prior to mixing of the polymer and nanoparticle components, optimizing characteristics that affect resistance of the final nanocomposite film by at least one selected from: varying the diameter of carbon nanotubes; varying a ratio of semiconducting to metallic carbon nanotubes; treating surfaces of the carbon nanotubes, and cross-linking the polymer to the carbon nanotubes.

Another embodiment of the invention provides a method of preparing a nanocomposite film which includes a carbon nanotube (CNT) and a non-conductive hydrogel polymer selected such that the film experiences a reversible hydrophobic/hydrophilic phase transition in response to a temperature change or a humidity change, the method including: forming a CNT-only film by filtering CNTs dispersed in a solvent; washing the CNT-only film with acetone to remove the solvent; coating the CNT-only film with the non-conductive hydrogel polymer thereby forming a CNT-polymer nanocomposite film by filtering the non-conductive hydrogel polymer solution through the CNT film; and forming contacts on the nanocomposite film for measuring electrical resistance, thereby preparing the nanocomposite film for connection as a sensor or circuit element.

In an embodiment of this method, the non-conductive hydrogel contains poly(N-isopropylacrylamide) or PNIPam. In an embodiment of this method the solvent used to disperse the CNT, and to dissolve the non-conductive hydrogel polymer is water. In an embodiment of this method a high degree of uniformity in the nanocomposite film is achieved, with an absence or reduced bundling of CNTs or aggregation of polymer, as observed with nano-scale resolution by scanning electron microscopy (SEM) or atomic force microscopy (AFM). In an embodiment of this method, forming the contacts for measuring resistance further comprises applying metal by masked electron beam evaporation or using conductive paste to attach wire contacts to the film. In an embodiment of this method, prior to forming a CNT-only film, optimizing the resistance of the nanocomposite film by at least one selected from: varying the diameter of carbon nanotubes; varying a ratio of semiconducting to metallic carbon nanotubes and treating surfaces of the carbon nanotubes. In an embodiment of this method, subsequent to coating the CNT-only film with the non-conductive hydrogel polymer, cross-linking the polymer to the carbon nanotubes.

Another embodiment of the invention provides a method of preparing a nanocomposite film that includes a carbon nanotube (CNT) and a non-conductive hydrogel polymer, so that the film experiences a phase transition characterized by a large volume change in an ambient condition of interest, and possesses a high thermal coefficient. The phase transition may, for example, be a reversible hydrophobic/hydrophilic phase transition in response to temperature change or a humidity change. The method of preparing the nanocomposite film may include: mixing water dispersed CNTs containing an anionic detergent such as sodium dodecyl sulphate (SDS) in an aqueous solution of the non-conductive hydrogel polymer containing SDS; drop casting the mixture of CNTs and the non-conductive hydrogel polymer onto a porous alumina substrate; allowing the solution to dry under room temperature and pressure conditions; and forming contacts on the nanocomposite film for measuring electrical resistance, thereby preparing the nanocomposite film as a sensing or circuit element.

In accordance with an important aspect of the invention, the amount or concentration of conductive carbon nanotubes in the composite film is relatively low, and the nanotubes are substantially uniformly distributed and dispersed, forming a network of nanotubes such that conduction proceeds through the nanotubes and their points of contact in the plane of the composite film. This involves tunneling from one nanotube to the next, through the intervening nonconductive polymer matrix material, at points of contact or near contact between nanotubes. Dimensional changes in the polymer matrix strongly affect the tunneling distance, hence activation energy needed for conduction through the network.

In various alternative embodiments of this method, the mass fraction of CNT in the nanocomposite film is greater than about 0.0001, or greater than about 0.0002, or about 0.0005, or about 0.001 or about 0.05. In an embodiment of this method the SDS in the dispersion of CNT in water and in the aqueous solution of non-conductive hydrogel polymer is about 1%. In an embodiment of this method, the non-conductive hydrogel further includes poly(N-isopropylacrylamide) abbreviated PNIPam. In an embodiment of this method, a high degree of uniformity in the nanocomposite film is observed by determining an absence or reduced bundling of CNTs or aggregation of polymer by scanning electron microscopy (SEM) or atomic force microscopy (AFM). In an embodiment of this method, forming the contacts for conducting electricity further comprises applying metal by masked electron beam evaporation or using conductive paste to attach wire contacts to opposite edges of the film. In an embodiment of this method, prior to mixing of the nanoparticles, the resistance characteristics of the nanocomposite film may be tailored and optimized by at least one selected from: varying the diameter of carbon nanotubes; varying a ratio of semiconducting to metallic carbon nanotubes; treating surfaces of the carbon nanotubes, and cross-linking the polymer to the carbon nanotubes.

Conductive nanocomposite films in accordance with the present invention provide many-fold greater sensitivity when operated to sense temperature changes, and their high absorbance and thin dimensions provide large responses and fast response times when used as a bolometer to detect light energy or the heating induced by impinging light. When operating near the hydrophobic/hydrophilic phase transition of PNIPam, sensor elements as described above may also be used to sense humidity with enhanced sensitivity.

Another embodiment of the invention provides a method of measuring a change in temperature, including: contacting at constant relative humidity, a nanocomposite film that includes a carbon nanotube (CNT) and a non-conductive hydrogel that experiences a reversible hydrophobic/hydrophilic phase transition in response temperature change, to an environment subject to changes in temperature; and measuring a change in electrical resistance of the nanocomposite film, thus measuring a change in temperature.

In an embodiment of this method the non-conductive hydrogel includes poly(N-isopropylacrylamide) or PNIPam. In an embodiment of this method, the nanocomposite film contacts to infrared light; and sensing infrared light by measuring temperature change resulting therefrom.

Another embodiment of the invention provides a thermal sensor device for sensing a change in temperature including: a nanocomposite film formed with carbon nanotubes (CNTs) and a non-conductive hydrogel polymer that experiences a reversible hydrophobic/hydrophilic phase transition in response to temperature change leading to a change in electrical resistance of the film; metal coated electrodes, such that the electrodes are situated adjacent to each other with a gap separating the electrodes, the nanocomposite film is situated across a gap between the electrodes, each electrode includes a wire, and forming a resistance measurement circuit; and an environmental housing chamber which is sealed and maintained at constant pressure and relative humidity; such that the electrodes and the nanocomposite film are located within the housing, and the nanocomposite film constitutes an electrical path for conducting electricity between the electrodes; such that sensing a change in temperature causes a change in resistance. The thermal sensor is suitable for detection of temperature changes in a range of temperatures from less than about 0° C. to at least about 45° C. For examples the thermal sensor can detect temperature changes such as an increase or decrease of about 2° C., about 3° C., about 4° C. in a range of about 0-10° C., 5-15° C., 10-20° C., 30-40° C., 10-30° C. and about 20-45° C.

In an embodiment of this device the electrodes comprise a metal coated substrate. In an embodiment of this method the substrate is at least one selected from the group consisting of: glass, teflon, plastic and quartz. In an embodiment of this method the non-conductive hydrogel comprises poly(N-isopropylacrylamide) or PNIPam. In an embodiment of this method the temperature change comprises illumination by infrared.

Another embodiment of the invention provides a method of measuring a change in relative humidity including: contacting at constant temperature, a nanocomposite film that includes carbon nanotubes (CNTs) and a non-conductive hydrogel that experiences a reversible hydrophobic/hydrophilic phase transition in response to a change in relative humidity, to environment subject to changes in relative humidity; and measuring a change in resistance of the nanocomposite film, thereby measuring change in relative humidity. In an embodiment of this method, the non-conductive hydrogel polymer comprises poly(N-isopropylacrylamide) or PNIPam.

Another embodiment of the invention provides a relative humidity sensor device for sensing a change in relative humidity including: a nanocomposite film comprising a carbon nanotube (CNT) and a non-conductive hydrogel polymer that experiences a reversible hydrophobic/hydrophilic phase transition in response to humidity change leading to a change in its electrical resistance; metal coated electrodes, such that the electrodes are situated adjacent to each other with a gap separating the electrodes, the nanocomposite is situated across the gap between the electrodes, each electrode includes a wire, and forming a circuit with a resistance meter; and an environmental housing chamber which is sealed and maintained at constant, pressure and temperature; such that the electrodes and the nanocomposite film are located within the housing, and the nanocomposite film constitutes an electrical path for conducting electricity between the electrodes; such that sensing a change in relative humidity comprises a change in resistance. The humidity sensor is suitable for detection of detection of humidity changes in a range of 0-100% relative humidity at a temperature of 15° C. For example, the humidity sensor can detect relative humidity percentage changes such as an increase or decrease of about 10%, about 20%, in a range of about 0-20%, 20-40%, 40-60% and about 60-100% relative humidity.

In an embodiment of this device, the non-conductive hydrogel polymer is poly(N-isopropylacrylamide) also referred to as PNIPam. In an embodiment of this method the electrodes comprise a metal coated substrate. In an embodiment of this method the substrate is at least one selected from the group consisting of: glass, teflon, plastic and quartz.

In greater generality, composites useful for improved sensor elements according to the invention may comprise a network of conducting and/or semiconducting particles which have measurable electrical resistance embedded in an insulating or non-conductive phase change polymer material, the type of nanoparticles and/or their concentration being optimized to provide an enhanced response of the nanocomposite film in a sensing region of interest near a phase transition point of the polymer.

Suitable nanoparticle materials for the conductive network may include, for example, carbon nanotubes (single- and multi-walled carbon nanotubes), cabon black, graphene, graphene oxide, metallic (silver, gold, copper, etc) wires and particles etc, as well as semiconducting nanoparticles (quantum dots), for example, formed of Si, PbS, Ge, ZnO, TiO2, or other known materials.

Suitable phase changing polymers include, for example, PNIPAM [Poly(N-isopropyl acrylamide)] as discussed above, various long-chain amidoamine derivatives, poly(methyl-glycerol), polyethylene glycol homopolymers, glycerol copolymers, poly(N-vinylcaprolactam), poly(methyl vinyl ether), poly(N-acryloyl-N'-propyl piperazine)], copolymers Poly(MEO2MA-co-OEGMA), α,α-disubstituted vinyl polymers, poly(N-n-propylacrylamide), Poly(N,N-diethylacrylamide), poly(N-cyclopropylacrylamide), poly(N-ethylacrylamide), methyl cellulose, and other polymers in which an appropriate transition has been identified.

As in the case of the PNIPam experiments reported infra, in which the phase change is assisted by water incorporation, the phase change in the above mentioned composites can be assisted by any suitable, corresponding or compatible solvent for the selected polymer system, such as water, methanol acetone, benzene, oils, tetrahydrofuran.

Applications for the nanocomposite sensors so produced include: temperature sensing, humidity sensing, breathalyzer/breath glucose sensing, sensing of an (organic) solvent, pressure/stress sensing, acoustic/ultrasound sensing. Persons skilled in sensor fabrication will understand that the actual sensed parameter will in general be a parameter that bears a direct relation to the properties of the composite nanofilm as explored herein, such as its light absorbance, temperature or hydration change, response to strain or pressure, resistance response, etc.

BRIEF DESCRIPTION OF DRAWINGS

These and other features of the invention will be understood from the description herein, taken together with the drawings illustrating features and properties of nanoparticle composites and sensing films formed therefrom, wherein:

FIG. 3C shows a Table with description, composition and carbon nanotube (CNT) mass fraction of nanocomposite samples of CNT-PNIPam;

DETAILED DESCRIPTION

Figure 1A:
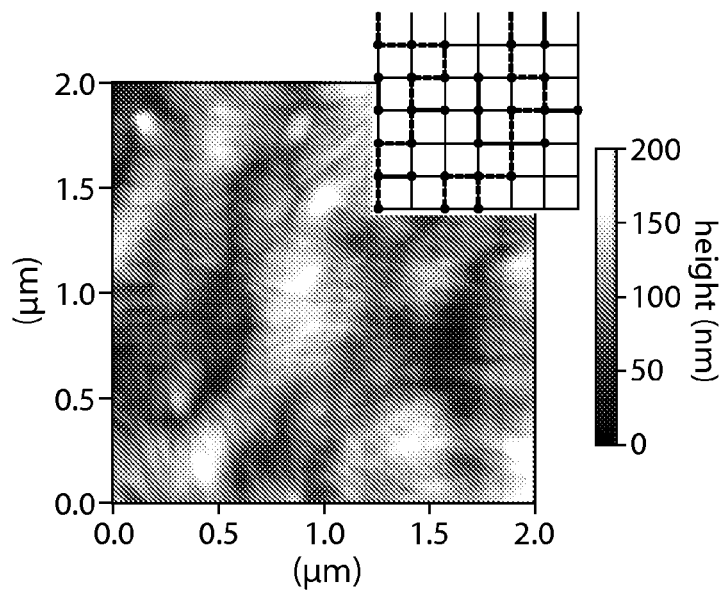
FIG. 1A is an image taken with an atomic force microscope of a carbon nanotube-PNIPam nanocomposite sample with 0.01% mass fraction of nanotubes.

The charge transport properties of films of randomly oriented carbon nanotubes can be interpreted as showing that transport is governed by hopping conductivity. Mott, Conduction in non-crystalline materials, Clarendon Press; Oxford University Press, 1987; Yanagi et al., ACS Nano, 4:4027-4032, 2010. In the case of carbon nanotube-polymer nanocomposites, structural thermal fluctuations contribute to the tunneling processes of electrons across sites in the carbon nanotube network, and a thermal fluctuation induced tunneling model has been applied instead to describe the temperature behavior of the conductivity in such films. Sheng et al., Physical Review Letters, 40:1197-1200, 1978. In these models, tunneling of electrons between carbon nanotubes depends exponentially on properties of the tunneling barrier and the temperatures. Applicant realized that this enhanced dependence may permit tuning the electrical properties of a nanotube-based conduction path via parameters such as the ratio of semiconducting to metallic carbon nanotubes, the mean carbon nanotube diameter, or the characteristics of the polymer host medium, all of which directly affect the tunneling barriers. Moreover, the choice of polymer medium offers the possibility of producing composites with enhanced response in particular regions of interest, as well as dynamically changing the properties of the composite by control of external parameters such as temperature, pressure, or applied electromagnetic field. As will be understood from the examples and results reported below, the selection of a polymer matrix that undergoes a phase transition near an ambient condition of interest, and fabrication of a nanoparticle composite sensing element with such a polymer, can result in an exceptionally large coefficient of the sensed response, for example, a TCR above 5% per ° C., when operated near the transition point.

Embodiments of the devices and methods herein were obtained from observations of response when introducing a phase change in material containing a random network of resistors, comprising a composite formed of carbon nanotubes (or other conductive material in particulate form) and a non-conductive phase change material such as a polymer that undergoes dynamic changes around the phase transition point, which result in strong changes in the conductivity of the composite, so that there is magnified sensitivity to the parameter(s) causing or affected by the phase change.

In examples exploring the magnitude of this effect, an embodiment of the device utilizes carbon nanotubes as the conductive material, and the phase change medium is the polymer PNIPam. PNIPam has a phase transition in its hydrophilicity which is accompanied by a large volume expansion or contraction. When PNIPam becomes hydrated (at lower temperatures) its volume increases (i.e. it swells). At higher temperatures the polymer dehydrates and shrinks. This phase change depends on both the temperature and the relative humidity. Thus, for values of temperature and relative humidity near the phase transition point, a small change in the temperature (or in humidity) causes swelling or shrinkage of the polymer, which in turn increases or decreases spacing between conductive particles contained in the composite and forming a conductive network between sensing electrodes. These small changes in particle spacing in turn appreciably change the electrical resistance of the network. This is because as the distance between the conductive particles becomes greater in the swollen state, the resistivity increases, and vice versa for the shrunken state.

In terms of the mechanism within these nanocomposites, it is envisioned herein that: conductive particles such as carbon nanotubes are suspended in the phase change medium, and thus form a random conductive network though which electrical current can travel. When connected across two electrodes for measuring the electrical resistance between two points of the nanocomposite, the electrical current travels across the various parallel paths in this random network. In each path the electrical current travels by tunneling from one conductive particle to the next one in the same path. The resistance of each path, and thus of the entire network, is greatly influenced by the distances between conductive particles, through which the electric current has to "tunnel" in moving between particles. For larger interparticle distances (swollen composite) the tunneling process is suppressed and the observed resistance quickly becomes very large. For smaller interparticle distances the tunneling process is enhanced and the observed resistance is smaller.

The phase transition of the matrix polymer need not necessarily be one which results in volume change. For instance, a phase transition that causes a change in the permittivity of the polymer matrix material will also affect inter-particle tunneling with similar effects. Thus the devices and methods described herein are based on the recognition that introducing a phase change in a structure (i.e. a nonconductive matrix material containing a network of conductive charge transport nanoparticles formed e.g., by conductive nanotubes in the exemplary embodiment), wherein resistance of the network depends upon tunneling of electrons across gaps occupied by the matrix or phase change material that exists between the nanoparticles, results in a highly sensitive composite material due to dynamic changes in the inter-particle spacing and/or electromagnetic characteristics that result from changes in the properties of the phase change material responding to environmental stimuli near its phase transition point.

This is illustrated by a series of experiments and investigations below.

Experimental Investigations

The temperature coefficient of resistance (TCR) is a basic figure of merit for bolometric sensing. In recent years, the increased need for infrared imaging has triggered the development of high TCR materials that have found application in devices for scientific, military and commercial use. Materials of higher TCR even than the popular vanadium oxides[1] have been available, including ones exhibiting metal-to-insulator phase transitions which display double-digit TCR values near room temperature.[2,3] High TCR is, however, not the only parameter that matters. Thermal mass, thermal conductivity, mechanical strength, and infrared absorption efficiency can be just as important for bolometric operation.[4] In these regards, thin films loaded with nanoparticles, and particularly with carbon nanotubes have much to offer.[5-8] Experiments reported herein demonstrate introduction of a phase-transition mechanism to this system resulting in an extraordinarily high TCR, up to several times higher than the present records in nanotube composites, such that enhanced uncooled IR bolometric detection can be readily observed in its as-is thin-film form, without applying any packaging or thermal engineering strategies.

A brief consideration of the physics of bolometric sensing provides a useful context for appreciating the measurements reported below. Bolometric infrared response can be found in many natural systems and increasingly now in man-made infrared sensing devices. In contrast to photocarrier generation across a bandgap, bolometers operate by converting the incident infrared radiation into heating of a detection body thereby inducing thermotransduction. As such bolometers can operate with extraordinary sensitivity without requiring cryogenic cooling. One partly analogous example from nature occurs in the venomous pit viper, which possesses a very thin sensory membrane suspended over an air chamber. The suspended membrane provides a fast thermal response to IR radiation, opening thermally-responsive ion channels to actuate neural transmissions for processing by the brain. Despite remarkable advances in materials for fabrication of uncooled bolometric sensing devices, the natural counterparts are still far superior in both sensitivity and in speed.

Carbon nanotubes were selected for investigation herein, as conductive nanoparticles for inclusion to impart a defined and measurable resistance to a polymer film for use as a sensor. Nanoparticle membranes have recently received considerable attention for their ability to sense infrared radiation in bolometric mode.[5-8,11] A single-walled carbon nanotube membrane can be modeled as a random network of resistors. In the case of high quality (high conductivity) and long nanotubes, the tubes themselves are conductive and the ensemble resistivity is dominated by the tube-tube junction resistances.[12] This resistance is quantum mechanical in nature[13-15] and depends exponentially on the spacing between the tubes and the temperature. This exponential dependence can be leveraged on by incorporating a medium that dynamically changes its volume in response to external stimuli. For the experiments reported herein we have chosen the phase-transition polymer poly(N-isopropylacrylamide) (PNIPAm) for its hydrophilic to hydrophobic phase-transition which occurs at a transition temperature near room temperature ($T_C \sim 32°$ C.).[16] In the hydrophilic state, which occurs below 32° C., PNIPAm can interact with moisture present in the surroundings and expand in volume by as much as one order of magnitude.[17] At higher temperatures, this hydrogel displays a tendency to expel moisture and become dehydrated, thereby restoring its original condition. This volume expansion/contraction enables an exponential response in quantum tunneling between nanotubes. The phase transition in hydrophobicity comes with a price—a greater dependence on environment control, so that the sensors would need to be sealed against moisture or be operated in a controlled environment chamber. Unless a seal is deployed, this might represent an additional engineering and packaging challenge in later stages of sensor development. On the other hand, the incorporation of fluid in the membrane may also provide an option for built-in cooling, mimicking the vascular fluidic cooling in the pit membrane of snakes that prevents afterimages and therefore effectively increases response/recycle speed of the sensing assembly. These potentials are not further explored here, however, and the focus and primary findings presented instead document the extraordinarily high TCR and bolometric IR responses, as well as the underlying mechanism, of a nanoparticle composite film sensing element.

A series of experiments were conducted to optimize a thin film nanocomposite sensor and determine relevant characteristics for improving performance.

Methods and Materials

Carbon Nanotube (CNT)-PNIPAM Nanocomposite Film Synthesis

Figure 4A:
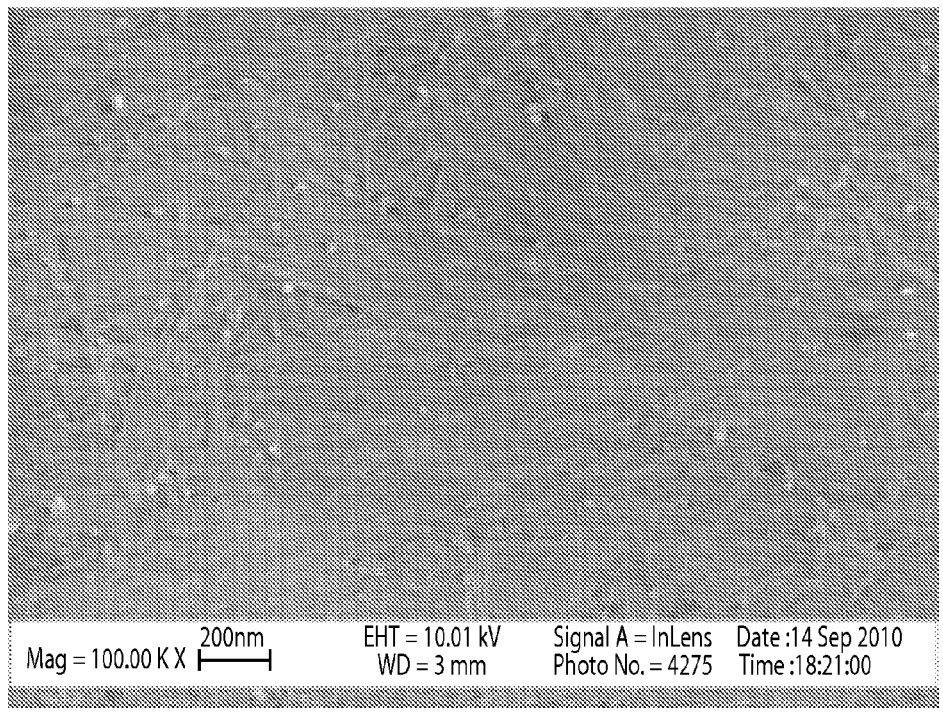
FIG. 4A is an SEM image of the surface of CNT-PNIPam sample D4 from Table I.
Figure 4B:
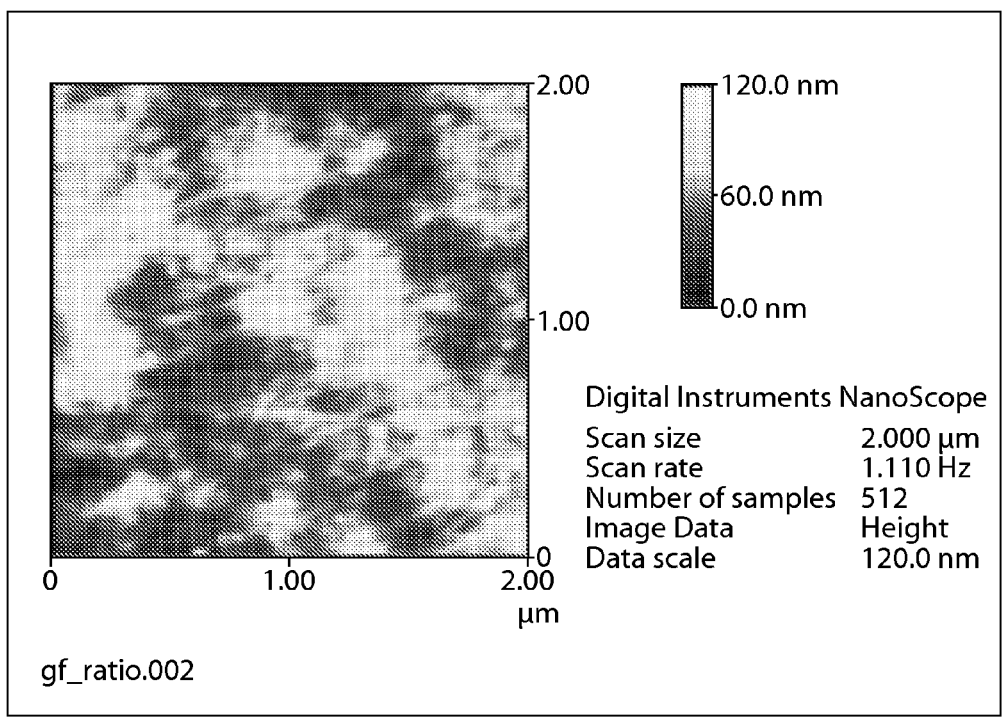
FIG. 4B is an AFM image of the surface of CNT-PNIPam sample D4 from Table I.

Thin-film samples of CNT-PNIPAM composite were prepared by drop casting a desired amount of an aqueous solution of CNTs and PNIPAM onto porous alumina substrates (Anodisk, Whatman) and allowing the solution to dry under room temperature and pressure conditions. The water-dispersed single walled CNTs containing 1% sodium dodecyl sulfate (SDS) (Nano-Integris) were dissolved in an aqueous solution of PNIPAM (Sigma-Aldrich) containing 1% SDS (Sigma-Aldrich). The compositions of various samples prepared and tested are given in TABLE I. This method produced highly uniform nanocomposite films without any observable bundling of CNTs or aggregations of polymer, as confirmed by both scanning electron microscope (SEM) (FIG. 4A) and atomic force microscope (AFM) (FIG. 4B) imaging of the samples. These Figures show sample D4 of TABLE I. After film formation, contacts were made to the samples either by masked electron beam evaporation of Pd or by attaching wire contacts directly to the films with silver paste. The two methods yielded similar results.

TCR Measurement

Figure 5:
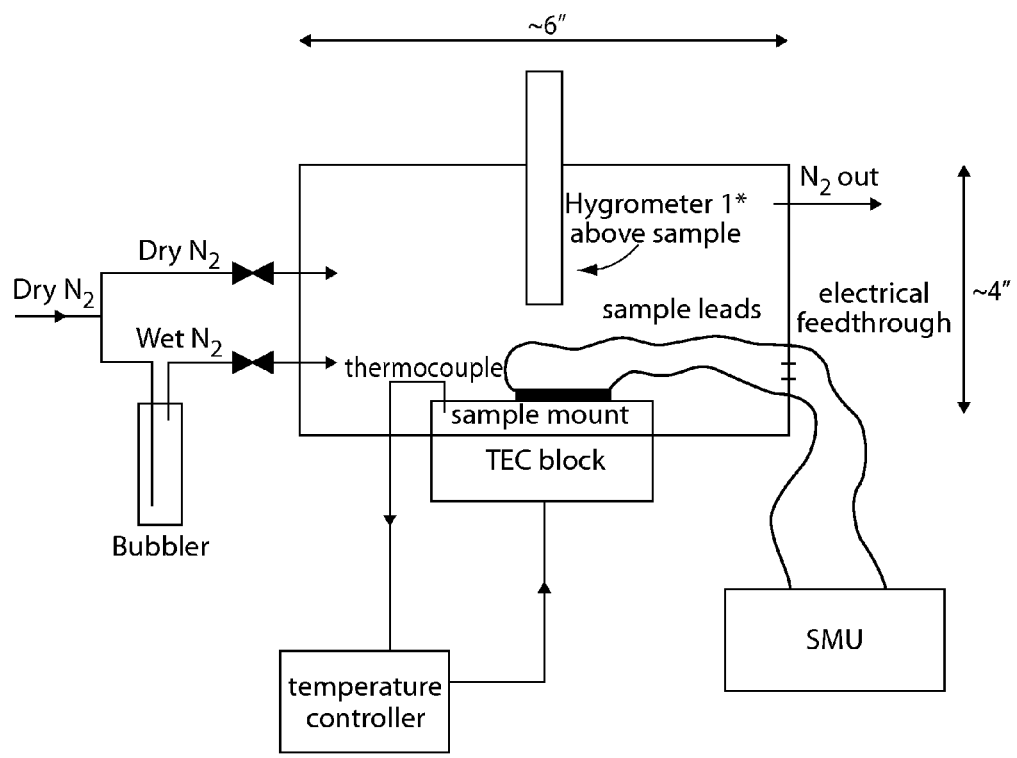
FIG. 5 is a drawing showing a schematic of the temperature and humidity controlled measurement chamber.

A schematic of the measurement setup is shown in FIG. 5. The sheet resistances of the samples were measured in a sealed environmental chamber kept at 21° C. and 1 atm. The relative humidity value inside the measurement chamber was controlled by adjusting the flow of wet and dry $N_2$ (wet $N_2$ was obtained by flowing dry $N_2$ through a water bubbler) and was monitored with a hygrometer. The samples were mounted on a thermoelectric heater/cooler plate inside the chamber. Sheet resistance measurements were taken at sample temperatures between 2 and 45° C. in increments of 1° C. A source measure unit (Keithley 236, Keithley) was used for the electrical measurements in two probe mode and a semiconductor parameter analyzer (HP 4145B, Hewlett Packard) was used for the four point probe measurements. The sample temperature was adjusted and controlled via a temperature controller (LDC 3722B, ILX Lightwave) and monitored by a thermocouple that was mounted onto the A1 block that served as sample stage in the chamber (see FIG. 5). Each set temperature was allowed to stabilize for two minutes before the measurement was taken. Initial testing revealed that both four and two-point probe methods yielded similar results, indicating that contact resistances were negligible. Subsequent measurements were then performed in two-point probe mode. The TCR values were calculated from the measured resistance data. Several samples made with similar composition were tested and all showed similar results.

Photoresponse Measurement; Details

Figure 2A:
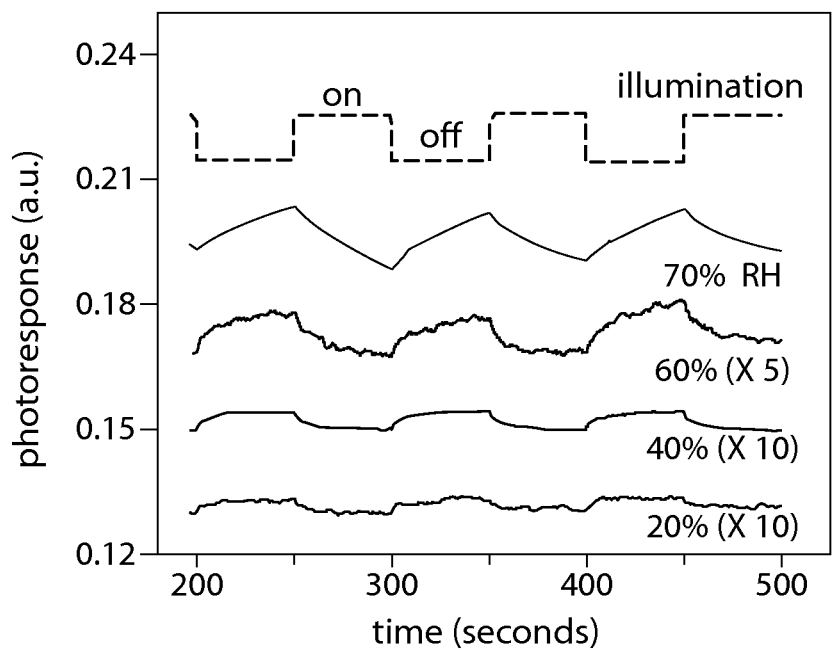
FIG. 2A is a line graph showing bolometric response measured at four relative humidity levels using a sample temperature of 15° C.
Figure 2B:
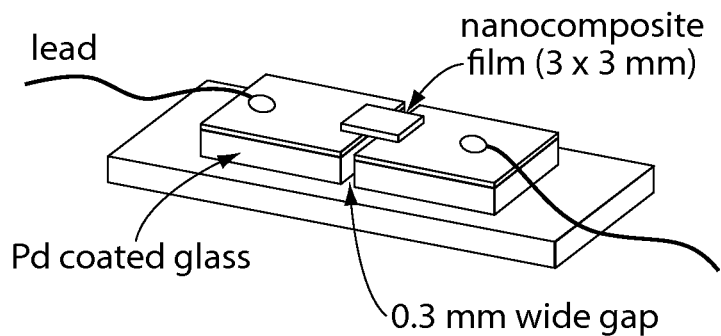
FIG. 2B is a schematic perspective drawing showing the device used for the measurements reported in FIG. 2A.

Films of ~1 μm in thickness with the same composition as sample A in TABLE I were suspended across an air gap of ~0.3 mm between two glass slides that were previously coated with 200 nm of palladium. Electrical contacts were made to the Pd covered glass without disturbing the suspended film, as shown in FIG. 2B. The width and length of the film were 3 mm and 3 mm, respectively, so that approximately 10% of the film area was suspended. The photoresponse was measured at constant sample current by measuring the voltage across the sample with a source measure unit (Keithley model 236).

Sheet Resistance as a Function of CNT Mass Fraction

The fluctuation-induced tunneling model employed herein takes into account the effects of local thermal fluctuations on the tunneling barrier heights. The conductivity is given by Equation 1 infra, has full form:

$$\sigma = \sigma_0 \exp\left(\frac{-T_1}{T_0 + T}\right), \quad (1A)$$

$$T_1 = wA\varepsilon_0^2 / 8\pi k, \quad (1B)$$

$$T_0 = 2T_1 / \pi \chi w, \quad (1C)$$

Where $\chi = \sqrt{2mV_0/h^2}$ and $\varepsilon_0 = 4V_0/ew$, with m and e the electron mass and charge, respectively, $V_0$ the potential barrier height, w the interparticle distance (i.e. the gap width between particles), and A the area of the junction.

As discussed by Connor et al[3] and references therein, Equation 1 can be written in the form $\ln \sigma \propto -w$. In terms of the sheet resistance (or the resistivity), it becomes $\ln R_{sheet} \propto w$. For a homogeneous dispersion of CNTs in the PNIPAM host medium, the gap width w and the CNT mass fraction p are related by $w \propto p^{-1/3}$ so we have:

$$\ln R_{sheet} \propto p^{-1/3} \quad (2)$$

Figure 7A:
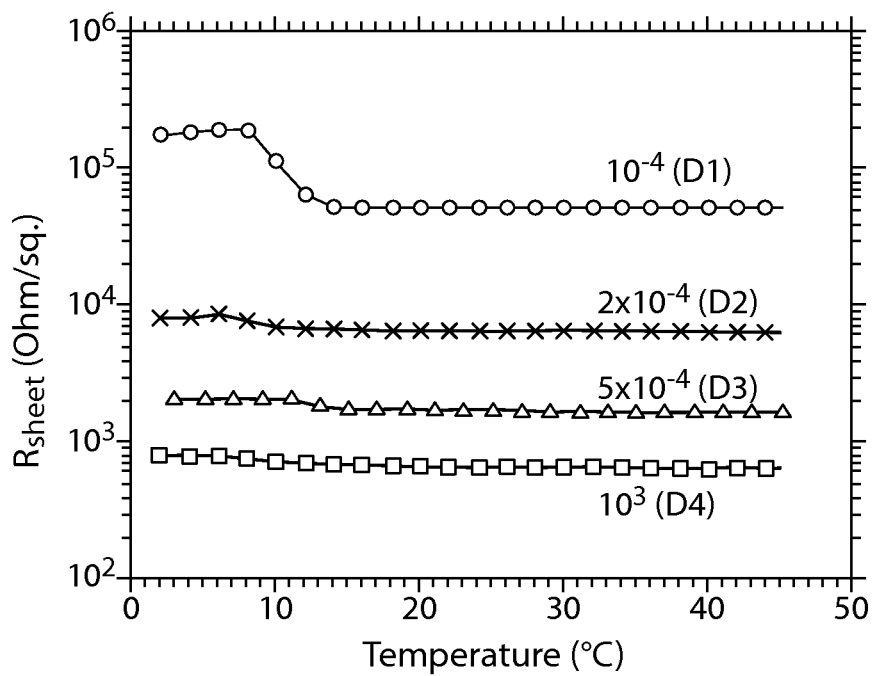
FIG. 7A is a line graph that shows sheet resistance change at four temperature values.
Figure 7B:
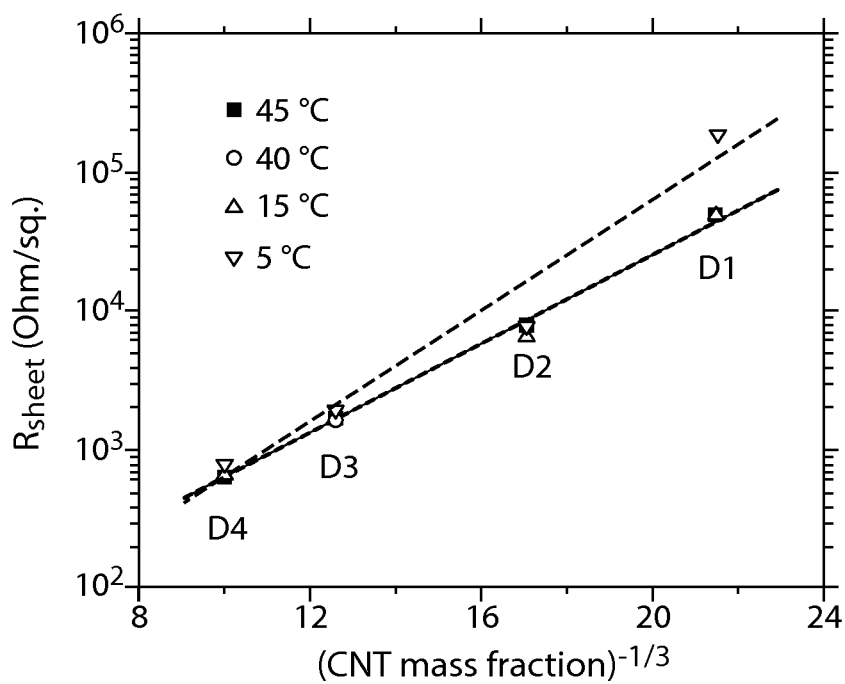
FIG. 7B is a line graph that shows the sheet resistance change at four carbon nanotube mass fraction values.

FIG. 7A shows the dependence of the sheet resistance on the temperature for nanocomposite sample with different CNT mass fraction (samples D1-D4 on TABLE I). The measurement was conducted at 60% relative humidity. The CNT mass fraction is indicated above each curve. The temperature behavior is consistent with the discussion in the main text. Below 15° C. the sheet resistance experiences a sharp increase due to the hydration of the polymer. The relative amount by which the sheet resistance increases becomes larger as the CNT mass fraction decreases. This behavior is expected because a relatively larger number of conduction paths are disrupted in the nanocomposites with smaller CNT mass fraction as the polymer expands. FIG. 7B shows the same data plotted as a function of CNT mass fraction. The lines are linear fits to the data points. The relation in Equation 2 is seen to be obeyed. Only at low temperatures and low CNT mass fraction does the relationship appear to not hold. This is illustrated by the data point corresponding to 5° C. for sample D1, which seems to fall abnormally above the other points. A linear fit to the data at 5° C. including this last data point yields the dashed blue line, which clearly deviates from the others.

Details of Photoresponse Measurement

Figure 8A:
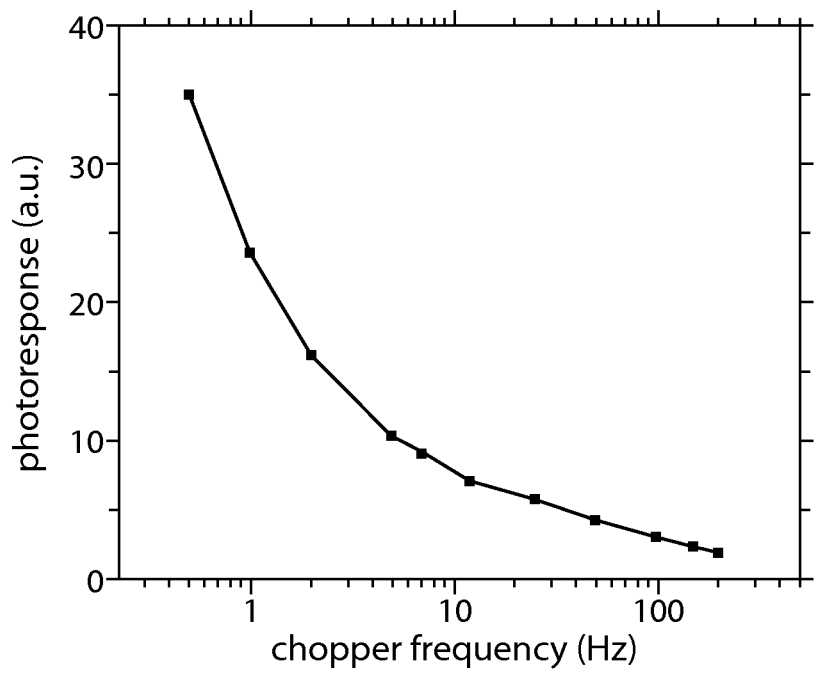
FIG. 8A is a line graph that shows change of photoresponse as a function of modulation frequency. Strong decay of photoresponse intensity is observed and is a characteristic of bolometric response.
Figure 8B:
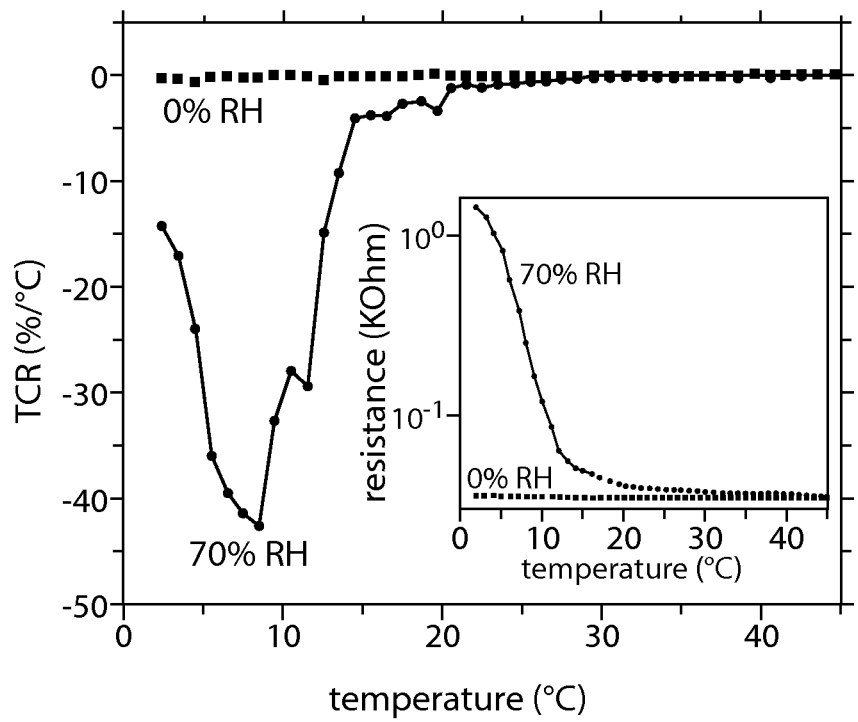
FIG. 8B is a line graph that shows the TCR and resistance change at two relative humidity values.

The frequency modulation measurements as shown in FIGS. 8A and 8B were done by measuring the sample voltage drop with a lock-in amplifier (Stanford Research Systems, model SRS 830). Data in FIG. 8 were taken with the sample nanocomposite film used for the photoresponse measurements in FIGS. 3A and 3B. FIG. 8A shows the behavior of the photoresponse as a function of modulation frequency of the source. The strong decay of the photoresponse intensity is a characteristic of bolometric response. The TCR and resistance data at two relative humidity values are shown in FIG. 8B.

Figure 1C:
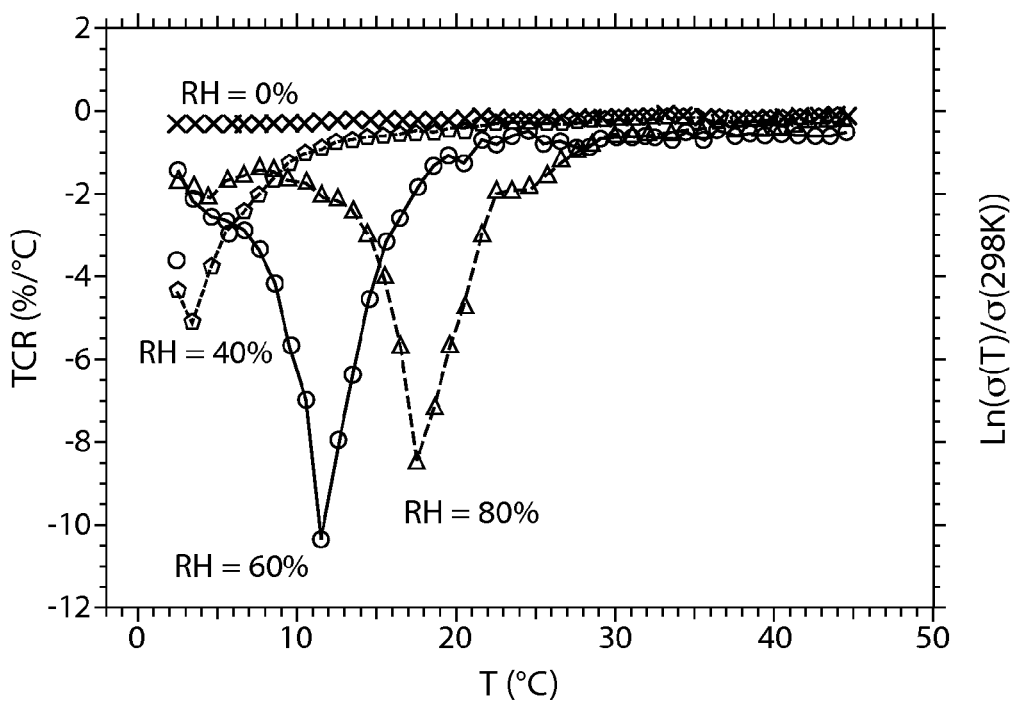
FIG. 1C is a line graph showing effect of temperature change on thermal coefficient of resistance (TCR) at four relative humidity levels. Peaks of large negative TCR were observed in the composites.
Figure 1B:
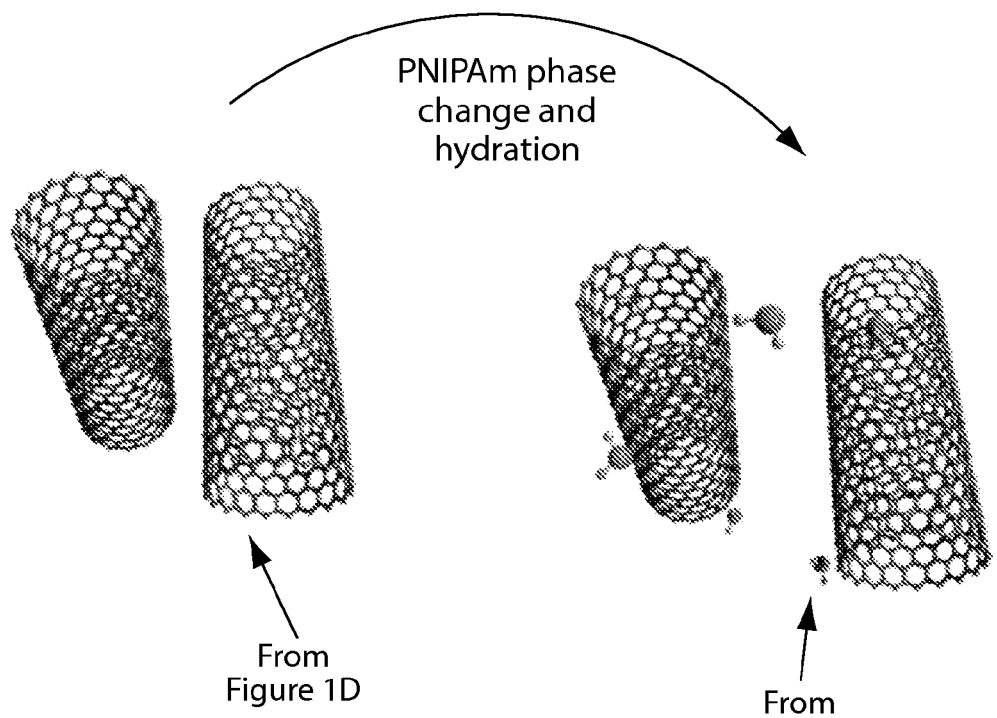
FIG. 1B is a drawing showing effects of hydration on spacing between nanotubes in the high temperature (HT) regime and the low temperature (LT) regime.
Figure 1D:
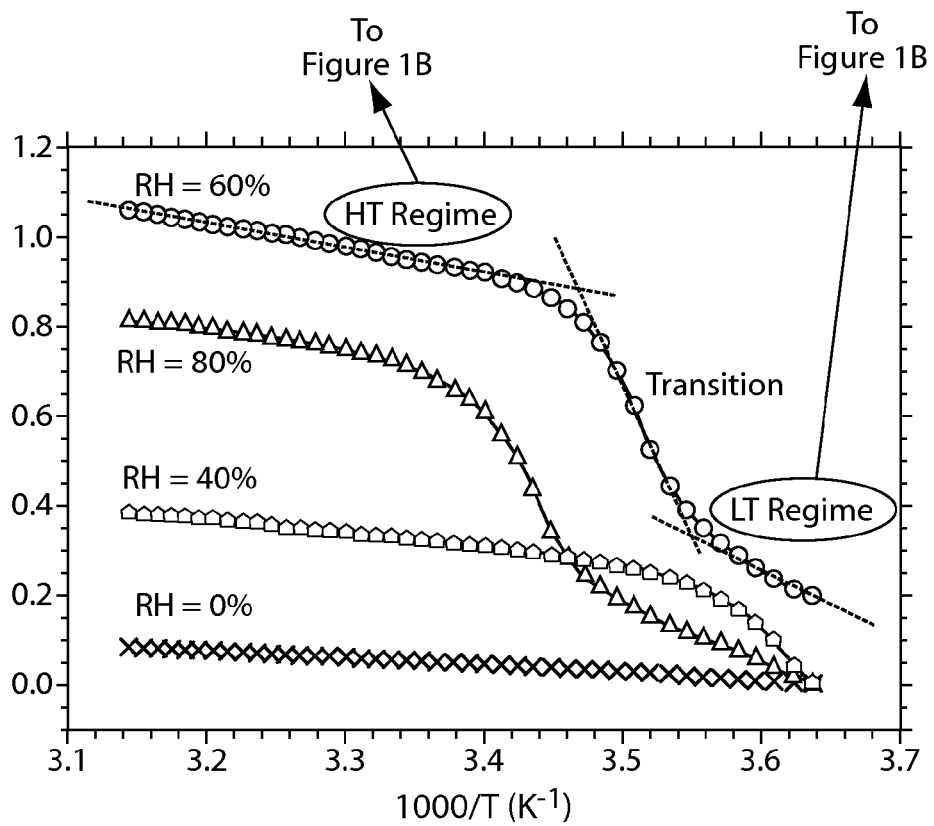
FIG. 1D is a line graph showing effect of varying the temperature on conductivity at four relative humidity levels.

Based upon the foregoing observations, a carbon nanotube composite sensor was designed to achieve high sensitivity bolometric sensing. FIG. 1A shows an atomic force microscope image of a carbon nanotube-PNIPAm nanocomposite sample film with 0.01% mass fraction of nanotubes. The nanocomposite can be modeled as a random network of resistors (illustrated in the inset) that undergoes a phase change in the conductivity as the polymer hydrates. FIG. 1B illustrates the effects of hydration on the spacing between nanotubes in each regime. FIG. 1C shows the temperature behavior of the TCR at various relative humidity levels showing the peaks of large negative TCR observed in the composites. FIG. 1D shows the temperature behavior of the conductivity at various relative humidity levels. The curve corresponding to 60% relative humidity in FIG. 1D is offset vertically for better viewing. The dashed lines serve as a guide to the eye in identifying the high temperature (HT), low temperature (LT) and transition regimes. The thickness of the film used for these measurements was ~500 nm. This provided a film of low thermal mass and high broadband absorbance effective to efficiently absorb incident light and convert infrared light to heat in the film or otherwise respond to ambient temperature.

As shown in FIGS. 1C and 1D, both the conductivity and TCR of the nanocomposite films exhibited a strong response to the sample temperature as well as to the relative humidity level in the ambient. At relative humidity values above around 40% and temperatures below $T_C$, the TCR assumed large negative values, many times greater than those that have been historically reported for carbon nanotube composites.[5-7,18] When the relative humidity in the measurement chamber was lower than 40%, the TCR values observed for all the samples tested were invariably below 0.5% per ° C. throughout the measured range of temperatures.

The occurrence of large TCR in these nanocomposites may be examined in the framework of a thermal fluctuation-induced tunneling model.[14] This model has been used in studies of other carbon nanotube-polymer nanocomposites[19-2] and found to describe well the temperature dependence of the conductivity at temperatures above ~45 K.[22] In this model the process of tunneling of electrons across the tube-to-tube potential barriers is described by Equation 1, infra, where $T_0$ and $T_1$ depend on the barrier parameters (e.g. the width, height, area, shape). $T_0$ is generally found to be small (~5 K),[14,21,22] and the behavior near room temperature is thus consistent with thermal activation, with an activation energy given by $T_1$.[14] Applying this model to our system reveals a phase transition-like behavior in the conductivity of the polymer-nanotube composite film as a function of temperature. The conductivity data in FIG. 1D exhibit two distinct regimes of thermal activation, as indicated by the dashed lines in the curve corresponding to 80% relative humidity value. In the high temperature (HT) regime the activation energy, which is proportional to the slope of the graph, is the smallest. The HT regime corresponds to the range of temperatures in which the nanocomposite is dehydrated. The larger conductivity of the samples in the HT regime suggests that the tunneling barriers are narrower in this regime, which is consistent with the composite being in a shrunken dehydrate state, in which the carbon nanotubes are on average closer together. In the LT regime, the decreased conductivity suggests that hydration and swelling of the nanocomposite have occurred. This process widens the tunneling barriers, which results in a larger value for the activation energy $T_1$. At 80% relative humidity, the activation energy increased from ~500 K in the dehydrated HT regime to more than 1500 K in the hydrated LT regime. The LT and HT regimes are connected by a transition region, as indicated in FIG. 1C. In this region the activation energy assumes its largest value (~5000 K) and becomes temperature dependent. The temperature dependence manifests itself as a nonlinear behavior in the semi-logarithmic plot of the conductivity within the transition region, and indicates that the tunneling barriers are dynamically changing with temperature in this region.

$$\sigma = \sigma_0 \exp\left(\frac{-T_1}{T_0 + T}\right) \quad (1)$$

Several mechanisms affect the shape and height of the tunneling barriers during the process of hydration/dehydration of the polymer. Chief among these are the swelling (shrinking) of the polymer as a result of hydration (dehydration), which causes the effective tunneling barrier to increase (decrease), along with the incorporation (secretion) of water molecules in the hydrogel structure. It is interesting to note that hydration of PNIPAm has also been observed to be accompanied by a decrease in the permittivity.[23,24] However, the observed increase in the sheet resistance with decreasing temperature suggests that swelling of the polymer (i.e. widening of the tunneling barriers) is the dominant mechanism in establishing the electrical properties of these films.

Figure 6A:
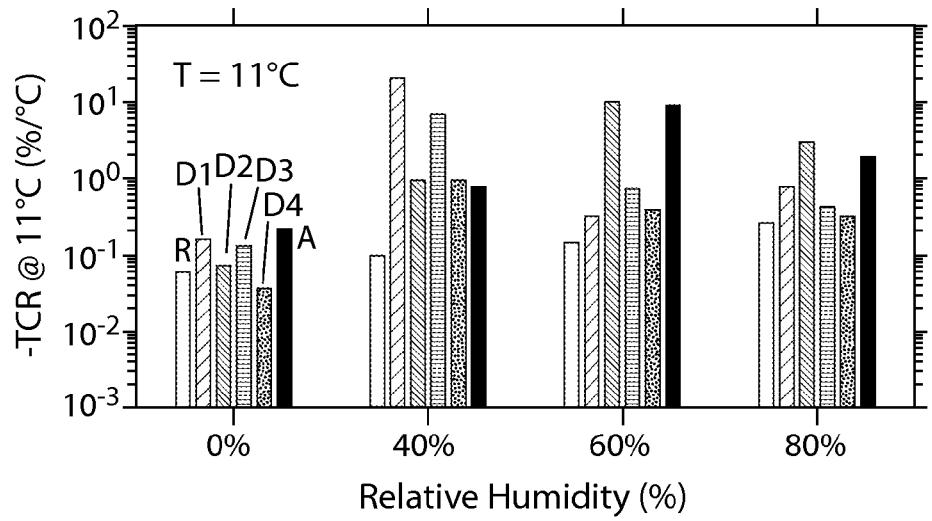
FIG. 6A is a bar graph that shows TCR at four relative humidity values at 11° C. for the samples described in Table I.
Figure 6B:
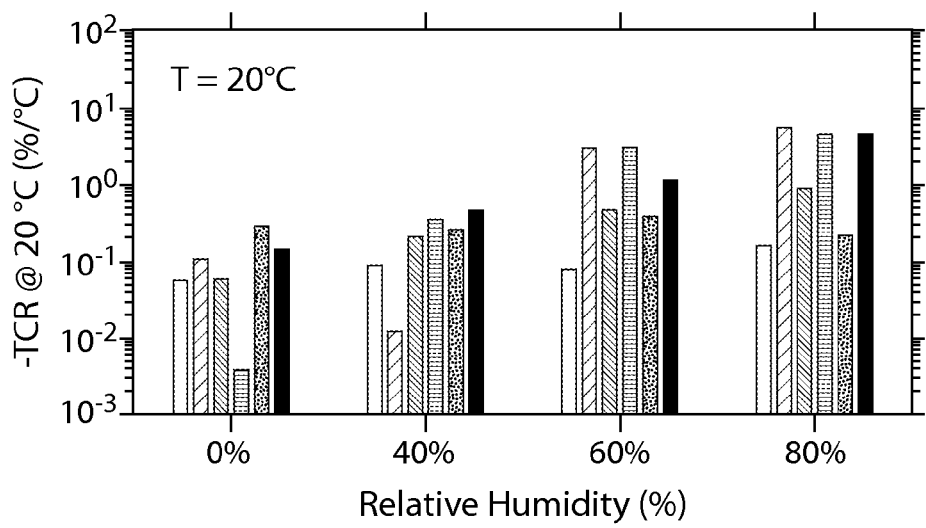
FIG. 6B is a bar graph that shows TCR at four elative humidity values at 20° C. for the samples described in Table I.

In all measured samples, a distinctive peak was observed to develop in the TCR vs. sample temperature curve. This peak occurred in the middle of the transition region and, within the accuracy of our measurement, the sample temperature at which the TCR peak occurred corresponded with the dew point temperature of water for the particular values of temperature and relative humidity of the atmosphere in the measurement chamber. The dew point represents the temperature at which condensation begins to take place; it depends on the sample and ambient temperatures as well as the relative humidity in the chamber. Although the largest observed TCR values occurred near the dew point of water, condensation was found not to be a prerequisite for large TCR or photoresponse values. As discussed further below in regard to FIGS. 6A and 6B, negative TCR values as large as −25% per ° C. at relative humidity values as small as 40% were observed at 11° C. (FIG. 6A), which is at least 4° C. above the dew point of water for these conditions. This is also observed in FIG. 6B, where TCR data taken at 20° C. and 60% relative humidity show TCR values as large as −3% per ° C. In this case the dew point of water is more than 7° C. below the sample temperature. The photoresponse data presented below also support this proposition.

These results demonstrate that the nanocomposites can interact with water vapor present in the surrounding atmosphere, and need not be wetted in a liquid water medium to experience hydration. Rather, the hydration process is governed by diffusion of water molecules from the surrounding atmosphere into the composite followed by incorporation of the water into the hydrogel structure, and swelling of the polymer.[25] In the HT regime, these processes must compete with the repulsion forces between the polymer and water molecules. At lower temperatures, however, the polymer acts favorably to incorporate water into the nanocomposite structure. The constant activation energy observed at temperatures below the dew point of water in FIG. 1C suggests that the hydration process reaches saturation only a few degrees below the dew point. For temperatures below the saturation point the nanocomposite no longer swells and settles into the LT regime with constant thermal activation energy, (i.e. a constant tunneling barrier) as described above.

In order to verify the effects of increased TCR on the photoresponse we measured the bolometric response of the nanocomposite as a function of temperature and relative humidity. A suspended film was illuminated by an infrared light emitting diode (LED, wavelength 880 nm) at a power density of 10 mW/cm$^2$. The LED was turned on and off by a square wave signal. FIG. 2A shows the change in sample voltage as a function of illumination measured at a sample temperature of 15° C. The amplitudes of the photoresponse for relative humidity of 60% and below are magnified for better viewing. The magnification is indicated in each trace. At 0% relative humidity, the corresponding change in sample resistivity between light on and off was $\Delta R/R \sim 0.13\%$. The nanocomposite's TCR value at the same conditions was −0.1%/° C. These values are comparable to those obtained in previous studies on bolometric responses of carbon nanotube films and carbon nanotube-polymer nanocomposites.[5-7] A significant increase was observed in the photoresponse and TCR as the relative humidity was gradually increased and the nanocomposite became hydrated. For example, at 78% relative humidity $\Delta R/R$ was observed to be greater than 6% between light on and off conditions, corresponding to a fifty-fold increase compared to the value at 0% relative humidity. The corresponding TCR also increased dramatically to −15.9%/° C. The changes with relative humidity of various quantities (all measured at 15° C.) are plotted in FIG. 3A. The photoresponse and TCR changed in a very similar manner and achieved comparable enhancements with hydration. Similar results were also observed in measurements taken at different temperatures at fixed relative humidity, shown in FIG. 3B. The similarity between the photoresponse and TCR curves suggests that the enhancement of the TCR in these nanocomposites can be almost entirely translated into increased bolometric response. Such finding opens the possibility for further exploration and optimization of this platform in the context of bolometric sensing. In particular, better thermal isolation of the sensing elements via improved device engineering, as well as strategies to seal the moisture content into the films in order to reduce the dependence on external conditions are likely to lead to even greater photoresponse enhancement.

Figure 3A:
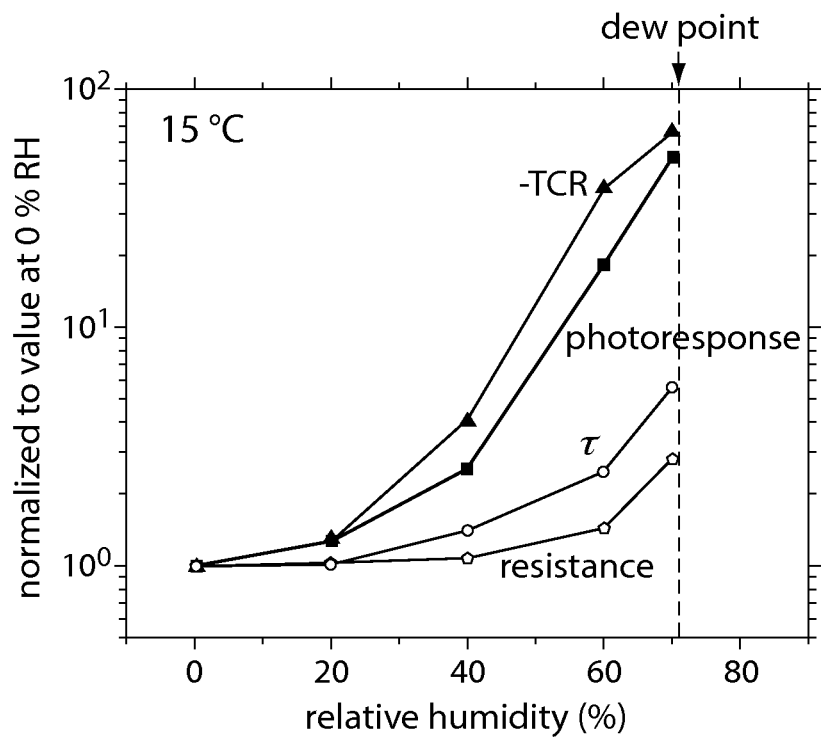
FIG. 3A is a line graph showing relative humidity change normalized to 0% relative humidity measured at 15° C.
Figure 3B:
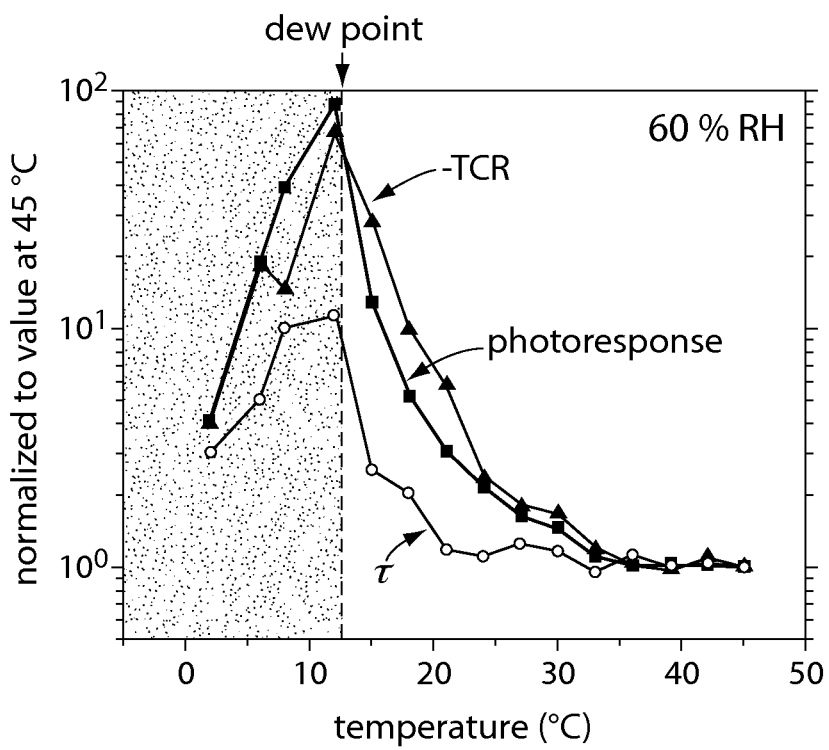
FIG. 3B is a line graph showing temperature change normalized to 45° C. measured at 60% relative humidity.

The dew point corresponding to the measurement conditions are indicated by the dashed lines in FIGS. 3A and 3B. Consistent with the model described above, both the TCR and the photoresponse achieved their maximum value at the dew point, and indicate the close relationship between the photoresponse and TCR. The photoresponsivity of thin film bolometers is also found to be proportional to the electrical resistance of the sensing element.[4] As illustrated in FIG. 3A, the electrical resistance experiences a much smaller relative increase with hydration than the photoresponse or the TCR. We consistently observed increases in the photoresponse at least one order of magnitude greater than the corresponding increase in the sample resistance. This indicates that the enhanced TCR provides a direct contribution to the photoresponsivity, which is far greater than that expected from an increase in sample resistance.

The process of hydration was also observed to lead to an increase in the time constant $\tau$ of the photoresponse, as seen in FIGS. 3A and 3B. This behavior is expected because the incorporation of water into the nanocomposite contributes to an increase of the heat capacity.[4] For bolometric sensors, the time constant can be written in the familiar form $\tau=RC$, where C is the heat capacity of the sensing element and R is the total thermal resistance coupling the sensing element to its surroundings.[4] As shown in FIG. 3B, the temperature behavior of $\tau$ is similar to that of the TCR and the photoresponse intensity; $\tau$ gradually increases as the sample temperature is decreased and the nanocomposite becomes hydrated, and peaks near the dew point. At its peak value, $\tau$ is about ten times larger than at 45° C., when the nanocomposite is dehydrated. These observations are consistent with the expected behavior of the heat capacity near a phase transition point. The foregoing discussion suggests that the value of $T_C$ in the case of a partially humid atmosphere coincides instead with the dew point temperature for given relative humidity and ambient temperature conditions.

The large TCR and photoresponses reported here are achieved in the vicinity of room temperature, making this nanocomposite attractive for uncooled infrared detection in the bolometric mode. In its unsealed form, the nanocomposite is also sensitive to relative humidity and may find applications in humidity sensing. The large TCR values observed are a consequence of PNIPAm's temperature-induced phase change. As such, our results suggest that further improvement of TCR may be achieved with optimization and device engineering. In particular, further engineering of the tunneling barriers via control of other parameters such as the average diameter of carbon nanotubes, the ratio of semiconducting to metallic carbon nanotubes, surface treatment of the carbon nanotubes, and cross-linking of polymer to the carbon nanotubes may be expected to produce further increases of TCR or extend the range of enhanced TCR. Other temperature responsive polymers, especially ones exhibiting phase transition behavior (or glass transitions) may be explored in the context of high TCR in nanocomposites with carbon nanotubes, and may also offer an alternative in cases where the humidity sensitivity may be undesirable. In other embodiments, the non-conductive polymer matrix material may for example be selected from among long-chain amidoamine derivatives, poly(methyl-glycerol), polyethylene glycol homopolymers, glycerol copolymers, poly(N-vinylcaprolactam), poly(methyl vinyl ether), poly(N-acryloyl-N'-propyl piperazine)], copolymers Poly(MEO2MA-co-OEGMA), $\alpha,\alpha$-disubstituted vinyl polymers, poly(N-n-propylacrylamide), Poly(N,N-diethylacrylamide), poly(N-cyclopropylacrylamide), poly(N-ethylacrylamide), methyl cellulose, or other polymers that exhibit a phase transition.

Further, while the experimental model described above employed composite film with carbon nanotubes, related results may be expected using other conductive nanoparticles, when the particle concentration, particle dimension, or other particle characteristics or parameters are suitably optimized to assure a strong tunneling dependence of the conductive pathways defined by the nanoparticles in a nonconductive matrix of a phase transition polymer in a nanocomposite film. In addition to single-wall carbon nanotubes, suitable nanoparticles may include multi-walled carbon nanotubes or mixtures thereof, carbon black, graphene, graphene oxide, metallic wires and particles (of silver, gold, copper, etc), as well as semiconducting nanoparticles (quantum dots), for example, nanoparticles of Si, PbS, Ge, ZnO, TiO2, or the like. Furthermore, while the carbon nanotubes themselves provide high broadband absorbance leading to heating of the film, absorbance may be tailored or enhanced when using other particle/polymer systems by inclusion of absorbing functionality or a dye in the polymer or particles.

Thus in optimizing the nanocomposite film as a sensor, one may employ a first approach, realizing that there is a tradeoff between optical absorption and electrical resistance regarding bolometer responsivity. Higher nanoparticle concentration implies more optical absorption but lower resistance, and vice-versa. The bolometer responsivity is proportional to the product of optical absorption, resistance, and TCR. Thus, for optimal responsivity one has to keep all these quantities as large as possible (within the limits of device implementation), hence the need for optimization.

A second approach, is to decouple optical absorption and resistivity altogether. In this sense, one would engineer the thermoresponsive nanocomposite to have the desired resistivity (and TCR) by tuning nanoparticle concentration and then separately adjust the optical absorption by one of the following:

(a)—placing the thermoresponsive composite (which presumably has low absorption) atop an IR absorbing layer, thus making a two layer sandwich structure in which one layer is electrically active and the other is optically absorbing. The two layers are in contact so that they are thermally coupled. For example, in vanadium oxide bolometers, the vanadium oxide (which has large TCR) has poor optical absorption and is thus typically placed atop a silicon nitride membrane which serves two roles: it absorbs IR light and heats up (thus heating also the vanadium oxide layer sitting atop it) and it serves as a suspending platform, which regulates thermal coupling with the surroundings.

(b)—another possibility would be inclusion of a separate species, one that absorbs IR but does not conduct electricity, into the nanoparticle-polymer nancomposite. This could be accomplished, for example, by certain IR responsive molecules in the form of a dyes or the like.

Advantageously, the nanoparticle/polymer composite films of the invention may be formed in bulk and may be diced into sensor elements of appropriate size, or may be affixed to patterned support circuits to form imaging arrays, sensors, or other circuit elements on semiconductor or MEMS patterned wafers or devices, thus offering an entirely new platform for fabrication of bolometric or other sensor elements. The nanocomposite materials may themselves be patterned, and their construction may be free of ionic impurities that would otherwise limit compatibility with existing semiconductor circuit fabrication platforms and processes. Thus, for example the film may be placed onto or suspended between already-deposited palladium electrode pads as described above, or palladium pads may be formed on the film to provide freestanding film sensor elements. Elements formed with high negative TCR values may be configured to operate as temperature-compensating resistors or other circuit elements to stabilize the temperature response of a sensor or circuit element, or may themselves be operated as high-sensitivity sensors.

The invention and representative embodiments being thus disclosed and described, variations thereof and improvements thereof will occur to those skilled in the art of microfabrication and sensor design, and all such variations and improvements are considered to be within the scope of the invention, as defined by the claims appended hereto and equivalents thereof. The contents of all references cited are hereby incorporated herein by reference in their entireties.

REFERENCES

Subrahmanyam, A., Reddy, Y. B. K. & Nagendra, C. L. Nano-vanadium oxide thin films in mixed phase for microbolometer applications. *Journal of Physics D-Applied Physics* 41, 195108, (2008).

Kolobov, A. V. et al. Understanding the phase-change mechanism of rewritable optical media. *Nat Mater* 3, 703-708, (2004).

Morin, F. J. Oxides Which Show a Metal-to-Insulator Transition at the Neel Temperature, *Physical Review Letters* 3, 34-36, (1959).

Liddiard, K. C. Thin-Film Resistance Bolometer Ir Detectors. *Infrared Phys* 24, 57-64, (1984).

Aliev, A. E. Bolometric detector on the basis of single-wall carbon nanotube/polymer composite. *Infrared Physics & Technology* 51, 541-545, (2008).

Itkis, M. E., Borondics, F., Yu, A. P. & Haddon, R. C. Bolometric infrared photoresponse of suspended single-walled carbon nanotube films. *Science* 312, 413-416, (2006).

Lu, R. T., Li, Z. Z., Xu, G. W. & Wu, J. Z. Suspending single-wall carbon nanotube thin film infrared bolometers on microchannels. *Applied Physics Letters* 94, 163110, (2009).

Jakubinek, M. B., White, M. A., Mu, M. F. & Winey, K. I. Temperature dependence of thermal conductivity enhancement in single-walled carbon nanotube/polystyrene composites. *Applied Physics Letters* 96, 083105-083108 (2010).

http://www.mapoflife.org/topics/topic_312_Infrared-detection-in-snakes/.

Gracheva, E. O. et al. Molecular basis of infrared detection by snakes. *Nature* 464, 1006-U1066, (2010).

Lu, R. T., Shi, J. J., Baca, F. J. & Wu, J. Z. High performance multiwall carbon nanotube bolometers. *Journal of Applied Physics* 108, 084305-084310 (2010).

Zhang, D. H. et al. Transparent, conductive, and flexible carbon nanotube films and their application in organic light-emitting diodes. Nano Letters 6, 1880-1886, (2006).

Mott, N. F. *Conduction in non-crystalline materials.* (Clarendon Press; Oxford University Press, 1987).

Sheng, P., Sichel, E. K. & Gittleman, J. I. Fluctuation-Induced Tunneling Conduction in Carbon-Polyvinylchloride Composites. *Physical Review Letters* 40, 1197-1200, (1978).

Yanagi, K. et al. Transport Mechanisms in Metallic and Semiconducting Single-Wall Carbon Nanotube Networks. *Acs Nano* 4, 4027-4032, (2010).

Schild, H. G. Poly(N-Isopropylacrylamide)—Experiment, Theory and Application. *Progress in Polymer Science* 17, 163-249, (1992).

Takahashi, K., Takigawa, T. & Masuda, T. Swelling and deswelling kinetics of poly(N-isopropylacrylamide) gels. *Journal of Chemical Physics* 120, 2972-2979, (2004).

Tarasov, M., Svensson, J., Kuzmin, L. & Campbell, E. E. B. Carbon nanotube bolometers. *Applied Physics Letters* 90, 163503-163506, (2007).

Barrau, S., Demont, P., Peigney, A., Laurent, C. & Lacabanne, C. DC and AC conductivity of carbon nanotubes-polyepoxy composites. *Macromolecules* 36, 5187-5194, (2003).

Pradhan, B., Setyowati, K., Liu, H. Y., Waldeck, D. H. & Chen, J. Carbon nanotube—Polymer nanocomposite infrared sensor. *Nano Letters* 8, 1142-1146, (2008).

Sankapal, B. R., Setyowati, K., Chen, J. & Liu, H. Electrical properties of air-stable, iodine-dope carbon-nanotube-polymer composites. *Applied Physics Letters* 91, 173103-173106 (2007).

Connor, M. T., Roy, S., Ezquerra, T. A. & Calleja, F. J. B. Broadband ac conductivity of conductor-polymer composites. *Physical Review B* 57, 2286-2294, (1998).

Garner, B. W., Cai, T., Ghosh, S., Hu, Z. B. & Neogi, A. Refractive Index Change Due to Volume-Phase Transition in Polyacrylamide Gel Nanospheres for Optoelectronics and Bio-photonics. *Applied Physics Express* 2, 057001-057004 (2009).

Zadrazil, A. & Stepánek, F. Investigation of thermo-responsive optical properties of a composite hydrogel. *Colloids and Surfaces A: Physicochem. Eng. Aspects* 372, 115-119, (2010).

Suarez, I. J., Fernandez-Nieves, A. & Marquez, M. Swelling kinetics of poly(N-isopropylacrylamide) minigels. *Journal of Physical Chemistry B* 110, 25729-25733, (2006).

Barenbrug, A. W. T. & Chamber of Mines of South Africa. Psychrometry and psychrometric charts. 3d edn, (Chamber of Mines of South Africa, 1974).

What is claimed is:

1. A nanocomposite sensing material comprising conductive nanoparticles and a non-conductive polymer matrix, wherein the polymer matrix experiences a reversible phase transition at a temperature or humidity transition region and the conductive nanoparticles are present in a concentration such that a conductive network comprised of the nanoparticles in the polymer matrix exhibits nonlinear tunneling conductivity for enhanced sensing response to a change in ambient condition, wherein the conductive network comprised of said nanoparticles in the composite exhibits a TCR substantially greater than its TCR outside of the transition region.

2. The nanocomposite of claim 1, wherein the non-conductive polymer matrix is selected from among PNIPam [Poly (N-isopropyl acrylamide)], long-chain amidoamine derivatives, poly(methyl-glycerol), polyethylene glycol homopolymers, glycerol copolymers, poly(N-vinylcaprolactam), poly (methyl vinyl ether), poly(N-acryloyl-N'-propyl piperazine), copolymers Poly(MEO2MA-co-OEGMA), α,α-disubstituted vinyl polymers, poly(N-n-propylacrylamide), Poly(N, N-diethylacrylamide), poly(N-cyclopropylacrylamide), poly (N-ethylacrylamide), and methyl cellulose polymers that exhibit a phase transition.

3. The nanocomposite of claim 2, wherein the non-conductive polymer matrix is the PNIPam [Poly (N-isopropyl acrylamide)].

4. The nanocomposite of claim 1, formed as a film and operated as a bolometric detection element.

5. The nanocomposite of claim 2, wherein the nanoparticles are particles selected from among one or more of single- or multi-walled or poly-crystalline carbon nanotubes, carbon black, graphene, graphene oxide, metallic wires and particles (of silver, gold, or copper), and semiconducting nanoparticles (quantum dots) of Si, PbS, Ge, ZnO, or TiO2.

6. The nanocomposite of claim 4, wherein the mass fraction of nanoparticles in the nanocomposite is a mass fraction between 0.0001 and 1.0% optimized to provide effective light energy absorption and heat transfer to surrounding polymer resulting in effective resistance characteristics for bolometric sensing with a high thermal coefficient of a response.

7. The nanocomposite of claim 6, characterized by highly uniform and non-aggregated particles and polymer, forming a film wherein the nanoparticles constitute a conductive network extending between electrodes with a resistance that varies in response to an ambient stimulus.

8. The nanocomposite film of claim 7, configured to operate as a sensor under an ambient condition near a phase transition of the polymer matrix.

9. A method of preparing a nanocomposite film comprising a nanoparticle component carbon nanotubes (CNTs) and a non-conductive polymer that experiences a phase transition such that the film operates as an effective sensor of temperature, humidity or a solvent or analyte, the method comprising:
   mixing liquid-dispersed nanoparticles containing a dispersant with a solution of the non-conductive polymer containing the detergent, and vacuum filtering through a membrane filter to form the nanocomposite film; and
   forming or attaching contacts on the nanocomposite film for measuring electrical resistance, thereby preparing the nanocomposite film as a sensor element, wherein the polymer matrix experiences a reversible phase transition at a temperature or humidity transition region and the conductive nanoparticles are present in a concentration such that a conductive network comprised of the nanoparticles in the polymer matrix exhibits nonlinear tunneling conductivity for enhanced sensing response to a change in ambient condition, wherein the conductive network comprised of said nanoparticles in the composite exhibits a TCR substantially greater than its TCR outside of the transition region.

10. The method according to claim 9, wherein the CNT concentration is less than about 0.05%.

11. The method according to claim 10, wherein the non-conductive polymer comprises a poly(N-isopropylacrylamide) (PNIPam).

\* \* \* \* \*